US006456262B1

United States Patent
Bell (10) Patent No.: US 6,456,262 B1
(45) Date of Patent: Sep. 24, 2002

(54) MICRODISPLAY WITH EYE GAZE DETECTION

(75) Inventor: Cynthia S. Bell, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 09/568,196

(22) Filed: May 9, 2000

(51) Int. Cl.[7] .............................. G09G 5/00; A61B 3/14
(52) U.S. Cl. ........................ 345/8; 345/472; 351/210; 351/209; 348/61; 348/63
(58) Field of Search .................. 345/8–9, 660, 345/667–671, 472, 472.1, 472.2, 788, 800, 698, 699; 348/53, 39, 61, 63; 351/209, 210

(56) References Cited

U.S. PATENT DOCUMENTS

| | | | | |
|---|---|---|---|---|
| 4,028,725 A | * | 6/1977 | Lewis ......................... 358/104 |
| 4,479,784 A | * | 10/1984 | Mallinson et al. ............. 434/43 |
| 4,513,317 A | * | 4/1985 | Ruoff, Jr. ..................... 358/133 |
| 5,731,805 A | * | 3/1998 | Tognazzini et al. .......... 345/156 |
| 5,857,120 A | | 1/1999 | Konishi ........................ 396/51 |
| 5,892,624 A | | 4/1999 | Kintz et al. .................. 359/637 |
| 5,905,525 A | * | 5/1999 | Ishibashi et al. .............. 348/39 |
| 5,912,721 A | * | 6/1999 | Yamaguchi et al. ......... 351/210 |
| 6,175,352 B1 | * | 1/2001 | Kay et al. .................... 345/103 |
| 6,315,273 B1 | * | 2/2002 | Lemelson et al. ........... 345/786 |

OTHER PUBLICATIONS

"ZCAM™ Depth Camera Enables a Host of Unique Applications Previously Unavailabe to Production Professional", 3DV Systema Ltd., pp. 1–3, Feb. 5, 2000.

Kay Talmi, Jin Liu, "Eye and Gaze Tracking for Visually Controlled Interactive Stereoscopic Displays", Heinrich–Hertz Institut, p. 1–5, Feb. 5, 2000.

"3–D Displays", Heinrich–Hertz Institut, pp. 1–3, Feb. 5, 2000.

* cited by examiner

Primary Examiner—Lun-Yi Lao
(74) Attorney, Agent, or Firm—Trop, Pruner & Hu, P.C.

(57) ABSTRACT

An electronic device may include a microdisplay in which a displayed image element may be selected by gazing upon it. An eye gaze detector may determine what the user is looking at at any given instance of time if the user looks at it for sufficient time. Once an image element is identified as being selected by being gazed upon, the screen display may be altered to change the appearance of the selected image element and the unselected image elements. For example, the selected image element may be brought into focus and other image elements may be blurred.

28 Claims, 12 Drawing Sheets

MICRODISPLAY WITH EYE GAZE DETECTION

BACKGROUND

This invention relates generally to microdisplays.

A microdisplay is a small display that normally cannot be viewed by the user unless the user's eye is proximate to the display. Thus, conventionally, a microdisplay is viewed with the user's eye constrained in an eyepiece for magnified viewing the small-sized display. The user may actually see a large virtual display, floating at the eyes' natural resting focus distance of about one meter.

Microdisplays have many advantages because the display takes up relatively small space in an electronic device. Microdisplays may be utilized in electronic devices such as cameras, telephones, and the like. In addition, microdisplays may be included in head-mounted devices wherein the display is positioned in front of the user's eye.

Microdisplays may also have low power consumption, the capability to display very high-resolution content, and may cost less than traditional displays. Microdisplays are advantageous for portable information devices because of their low power consumption, portability and pocketability.

Manually operated controls on the portable electronic device may be awkward to use in conjunction with the microdisplay. This is because the microdisplay needs to be held up to the user's eye. When the microdisplay is in position for viewing, it may make manual manipulations difficult to perform because the user's head and nose may be in the way.

Existing microdisplays convey an impression of a flat, two dimensional field, viewing such displays may be visually uninteresting and may result in fatigue.

Thus, there is a need for better ways to use devices with microdisplays.

DETAILED DESCRIPTION

Figure 1:
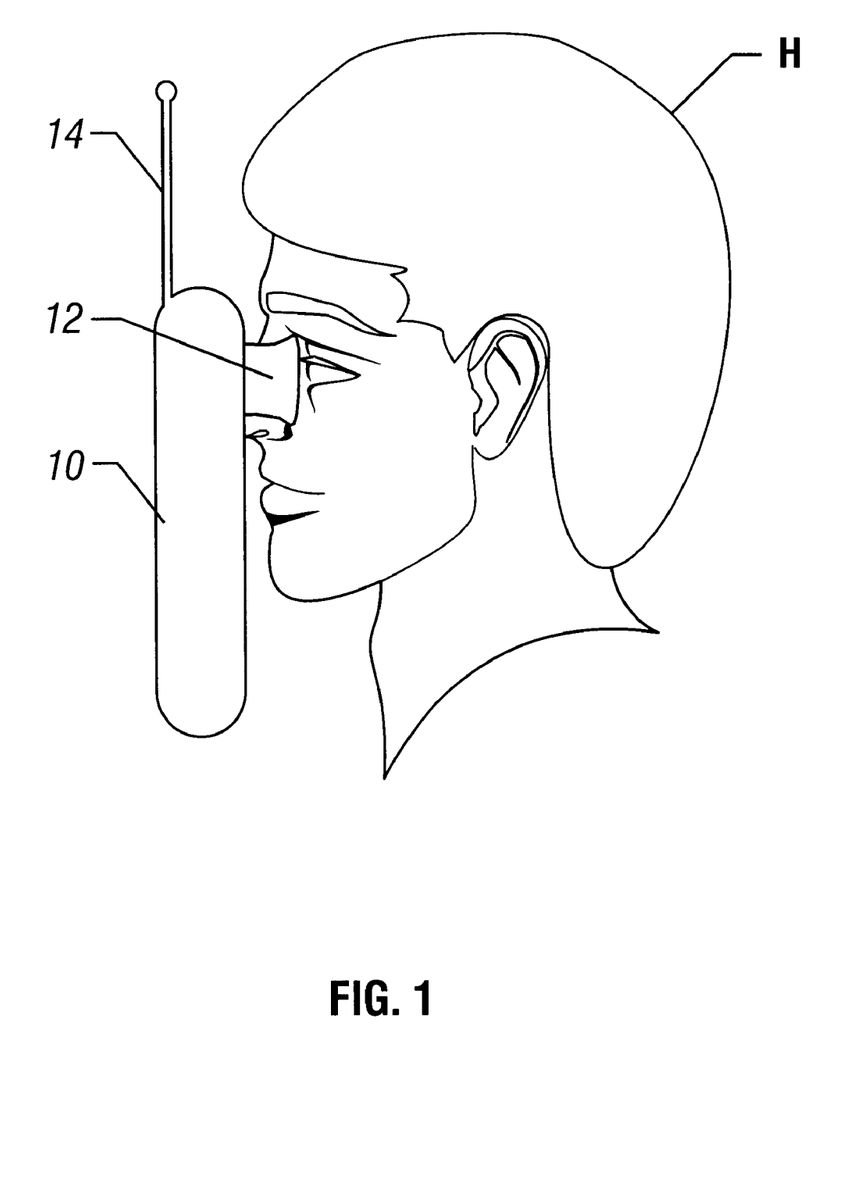
FIG. 1 is a side elevational view of one embodiment in the present invention in position in front of the user's eye in accordance with one embodiment of the present invention.

Referring to FIG. 1, in accordance with one embodiment of the present invention, an electronic device 10 may be fitted with a microdisplay that is viewable through an eyepiece 12 positioned proximate to the user's eye. With the user's head "H" arranged near the top of the electronic device 10, the user can view a microdisplay that is mounted within the electronic device 10.

The electronic device 10 is illustrated as being a cellular phone having an antenna 14. However, the present invention is applicable to a wide variety of portable electronic devices including cameras, personal digital assistants, appliances, games, and calculators, as just a few examples. In general, these devices may have an electronic microdisplay controlled by a processor-based system.

Microdisplays are well known and may use a wide variety of technologies. For example, liquid crystal over semiconductor (LCOS) technologies may be utilized to form a liquid crystal display of very small size directly on an integrated circuit. The integrated circuit may include the display as well as other components such as a processor, as one example.

Figure 2:
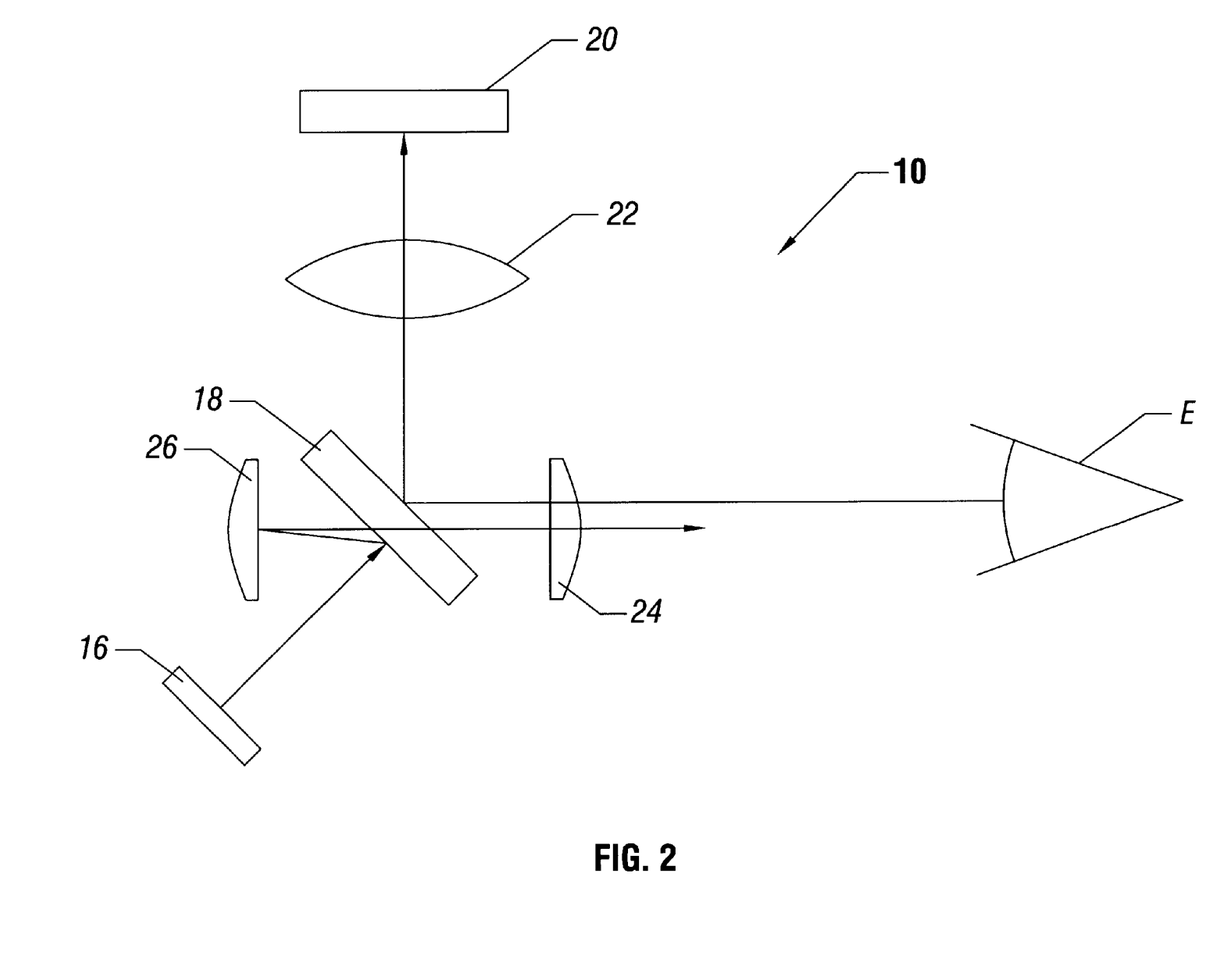
FIG. 2 is a schematic side elevational view of one embodiment of the optical system for the device shown in FIG. 1.

An optical system 10, shown in FIG. 2, may be utilized in one embodiment of the present invention. The user's eye, indicated at "E," is positioned in the eyepiece 12 where the user views the microdisplay 16. The microdisplay 16 may be viewed through a folded optical system, to enhance compactness, which may include a front lens 24 and a back lens 26. The front lens 24 may be useful for image element magnification and the back lens 26 may be useful for image element magnification and reflection.

Figure 3:
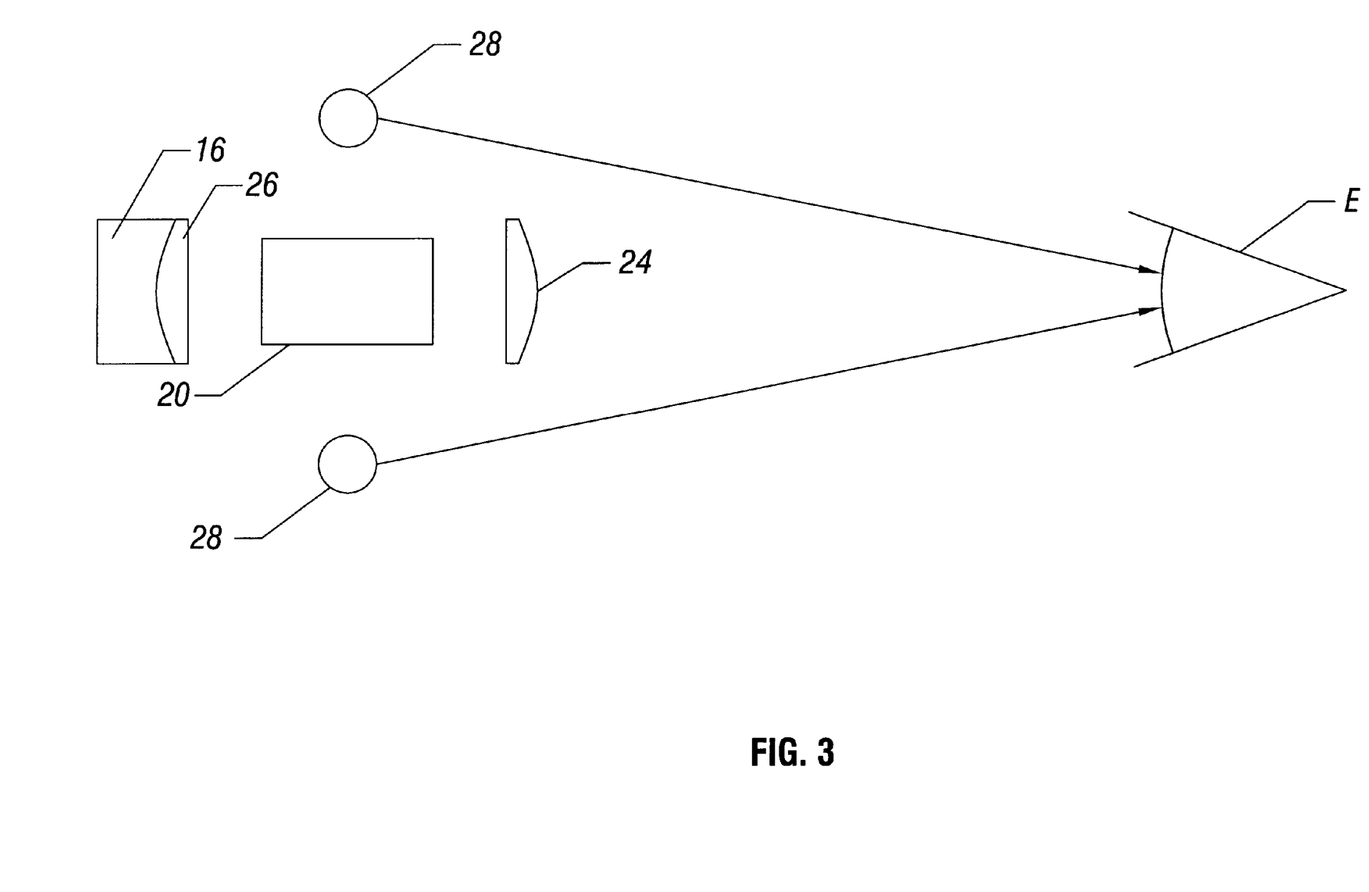
FIG. 3 is a top plan view of one embodiment of the optical system for the device shown in FIG. 1.

In FIG. 3, the user's eye E is also positioned in the eyepiece 12 where infrared light may be reflected off the user's eye E and used to determine what the user is looking at. A pair of infrared eye illuminators 28 may be arranged to emit infrared light into the user's eye E. The infrared light reflections from the user's eye E may be reflected off a dichroic mirror 18, as shown in FIG. 2.

The dichroic mirror 18 is wavelength selective. It tends to pass the visible and reflect the infrared light portion of the spectrum according to the direction arrows shown in the diagram. The front lens 24 may also be useful for eye gaze detection.

An infrared imaging subsystem 20 may capture infrared light that is reflected off the user's eye E and the dichroic mirror 18. A capture lens 22 may be positioned between the infrared imaging subsystem 20 and the dichroic mirror 18. The eye image is recorded on the infrared imaging subsystem 20 through the capture lens 22. The infrared imaging subsystem 20 and infrared eye illuminators 28 may constitute a gaze data module 32.

Figure 4:
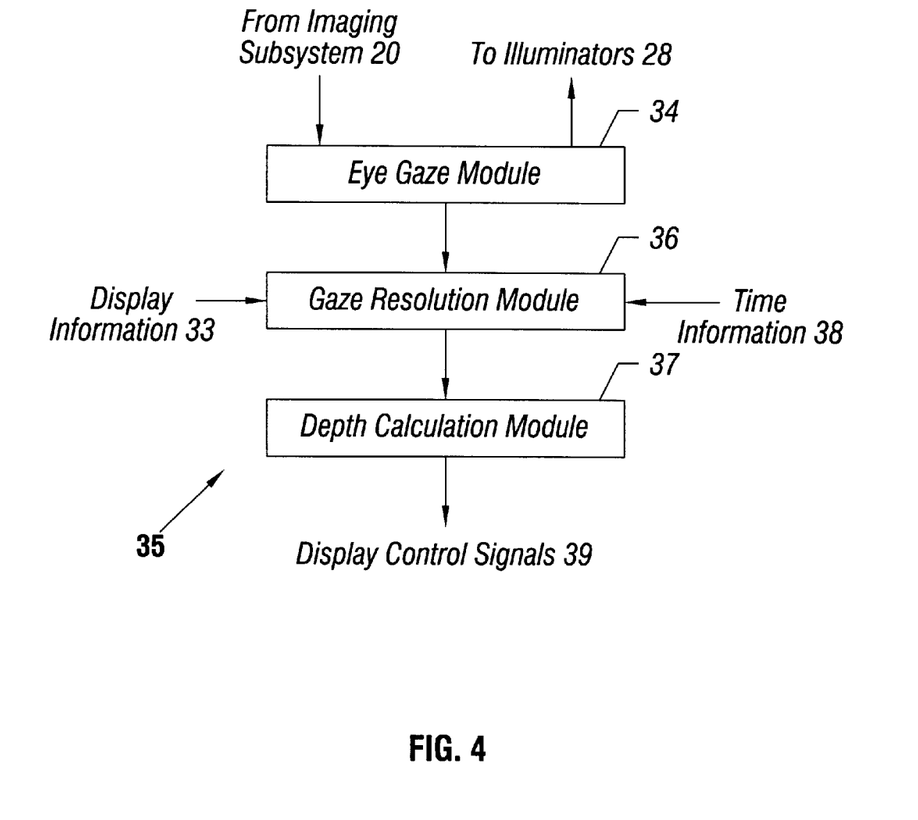
FIG. 4 is a depiction of software in one embodiment of the invention.

Software 35, shown in FIG. 4, determines what the user is looking at and adjusts the display accordingly. The eye gaze module 34 receives gaze data indicating what the user is looking at from the imaging subsystem 20. In turn, the eye gaze software module 34 generates control signals for controlling the illuminators 28. The module 34 may also provide information to a gaze resolution module 36, which provides information to a depth calculation module 37.

The eye gaze module 34, which may possess images reflected from eye surfaces known as the Purkinje images, may spatially resolve the user's gaze direction from points receiving from points receiving the strongest infrared reflections. Depending on the amount of eye relief and the size of the exit pupil, the eye gaze module 34 may also detect the sclera-iris boundary.

The gaze resolution module 36 may determine if the spatial position of the user's gaze developed by the module 34 is coincident with any user selectable activation point displayed on the microdisplay 16. If the user's gaze coincides with a user selectable activation point, the depth calculation module 37 may determine an altered depth of field based upon that information.

Timing information 38 may be utilized by the gaze resolution module 36 to determine if the user has gazed upon an activation point on the microdisplay 16 long enough to indicate a voluntary activation request. A display controller (not shown in FIG. 4) may provide display information 33 to the gaze resolution module 36 about the x y coordinates for image elements displayed on the microdisplay 16. Moreover, the depth calculation module 37 may generate display control signals 39 to adjust the altered depth of field on the microdisplay 16 based on the user's gaze.

Tracking the various features of the eye, including determining the sclera-iris boundary, the iris-pupil boundary, and tracking infrared reflections from the cornea and the lens surfaces, commonly known as the Purkinje images, are all well known. These features may be tracked to determine what the user is actually looking at. In particular, the Purkinje image element measurements are well suited to the type of eye gaze measurement possible with microdisplays.

A number of techniques are known for coordinating what the user is looking at with what is displayed in front of the user. For example, in U.S. Pat. No. 5,857,120, the x y coordinates of a watching point are determined. The accumulated stagnant time that the viewer gazed at each watching point is also determined. The eye movement trajectory between fixation periods is tracked. Likewise, the frequency of gazing at various watching points may be evaluated. A weighting may be developed to give emphasis to the points watched closest to the time of a pertinent activity, such as a picture capture request. A correlation factor may be developed between subsequent watching points.

Figure 5:
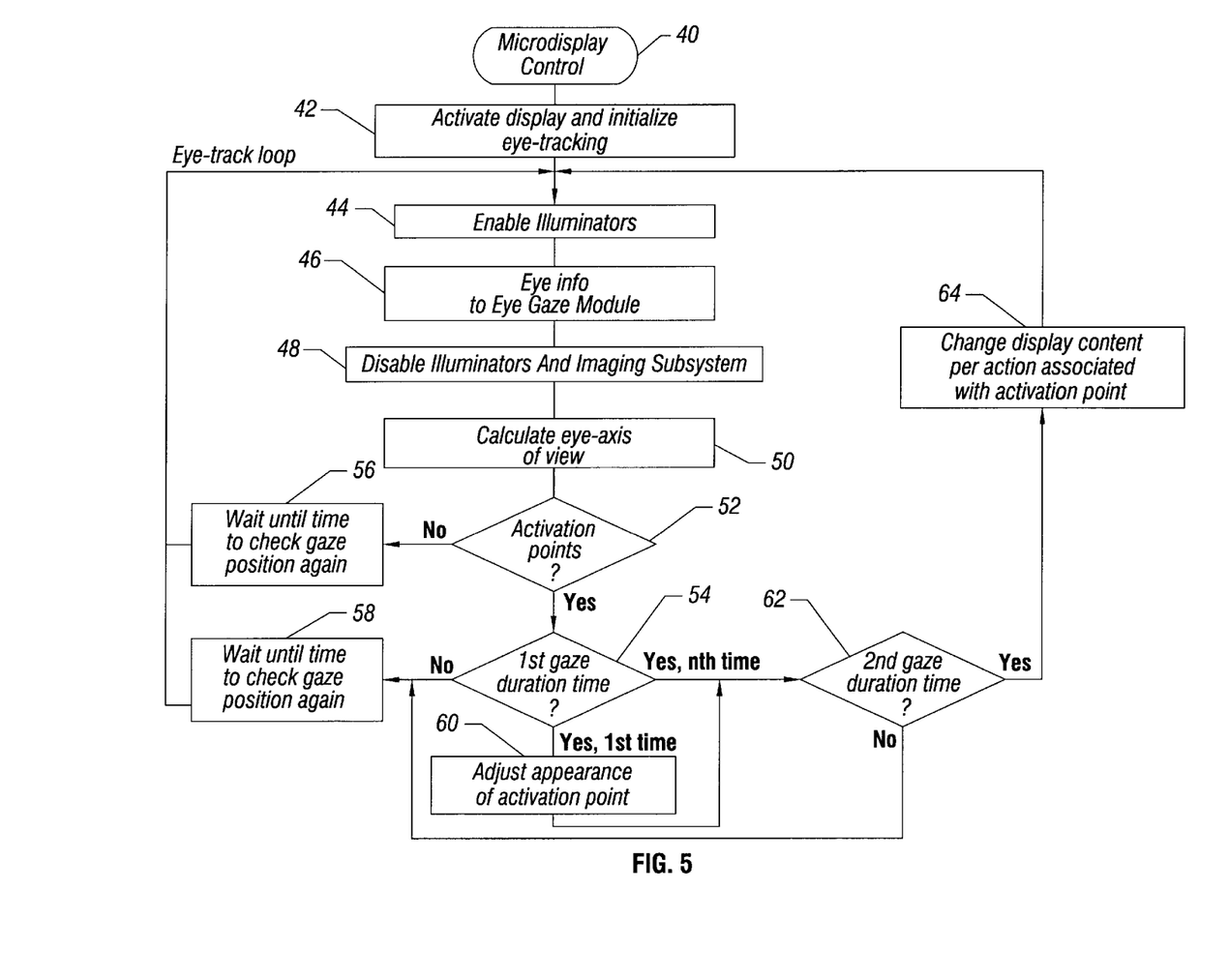
FIG. 5 is a flow chart for software useful in one embodiment of the invention.

Software 40, shown in FIG. 5, may be utilized to control what is displayed on the microdisplay 16 in response to what the user is looking at. The software 40 begins by activating the microdisplay 16 and initializing eye tracking, as indicated in block 42. The illuminators 28 are enabled to detect and process the eye reflection image, as indicated in block 44. The sclera-iris boundary may be detected by the imaging subsystem 20 in one embodiment of the present invention, as indicated in block 46. Additionally, the first Purkinje image x y positions are sent to the eye gaze module 34, as also indicated in block 46.

Thereafter, as shown in block 48, the illuminator 28 and imaging subsystem 20 may be disabled. The gaze resolution module 36 then calculates the eye axis of view or gaze, as indicated in block 50. If the eye axis of view intersects with a known activation point being displayed, as shown in diamond 52, it is assumed that the user may be indicating that he or she wishes to select the gazed upon activation point. A time threshold may be useful to separate field voluntary eye allocation periods from involuntary eye saccades, in which the eye rapidly transverses the visual field. However, the threshold time may be short enough to be very natural to the user.

A check in diamond 54 determines whether this is the first time that the user has gazed at the activation point. If it is, and the user has gazed at the activation point for more than a threshold period, the appearance of the activation point is adjusted in a first way to give the user feedback that his or her gaze is being assessed, as indicated in block 60.

After the user has gazed at the activation point a given number of times, such as two, and the minimum threshold time per gaze is met, as determined in diamond 62, the displayed content is changed as indicated in block 64.

If the user's gaze has not met the first or second voluntary gaze duration time threshold, the system waits for another opportunity to check the gaze position, as indicated in block 58. Similarly, if the user's eye gaze did not intersect with a known activation point (diamond 52) the system goes back into a waiting mode, as indicated in block 56.

In one embodiment of the invention, the display alterations may be utilized as an indication to the user that a highlighted activation point has been selected. For example, the activation point selected may be brought into clear focus, whereas other image elements on the same display 16 are blurred. In effect, the gazed upon activation point has the depth of field centered around it, whereas the other displayed image elements may be at the out of focus and are out of focus. That is, the image element the user is interested in automatically defines the depth of field of the display 16 and the other image elements are thereby defined as being in front of or in back of the current the depth of field. As a result, when the user is viewing the microdisplay 16, the user may be given a three-dimensional viewing effect. Thus, the selected activation point is identified as being clearly in focus compared to other items.

The assignment of the depth of field, which may be centered around various displayed image elements, can be accomplished in a number of ways. First, each of the displayed image elements may have pre-stored x y coordinates. This is particularly viable in cases when the image element is generated by the display's own processor-based system. In such case, the programmer may assign x y coordinates to each of the image element. Thus, the display 16 may assume a depth of field before any image element is selected and another depth of field thereafter. In effect, some image elements may be blurred while the image element gazed upon is enlarged and placed in focus.

Second, in other embodiments, depth of field information may be conveyed with information that is received from a video source. For example, depth information is encoded for each object captured by cameras made by 3DV Systems, Ltd. (Yokneam 20692, Israel). Those cameras produce a video stream for television shows and movies. This real time 3D camera employs a scanning laser beam and a time-of-flight detection system to capture the third dimension.

The 3DV Systems' device captures video with a camera having x, y and z information. To use natural video context, the depth of field (z information) introduced by the camera's taking lens may be taken into account. This can be managed by recording a scene multiple times or simultaneously with multiple cameras. In each recording, the taking lens is focused at a different subject distance so that in focus image element slices of the scene are available, each slice at a different focal distance. When the user gazes upon a specific image element, the recording with that image element in best focus is retrieved and displayed.

In sum, once it is known what the user is gazing at, and the depth of field information has been obtained, the item gazed at can be automatically placed in the center of the depth of field and other objects may be placed out of the depth of field and thereby automatically blurred.

Alternatively, image elements that are gazed upon may be enlarged relative to other image elements. In some embodiments, gazed upon image elements may be more focussed and enlarged relative to image elements that are not gazed upon.

Figure 6:
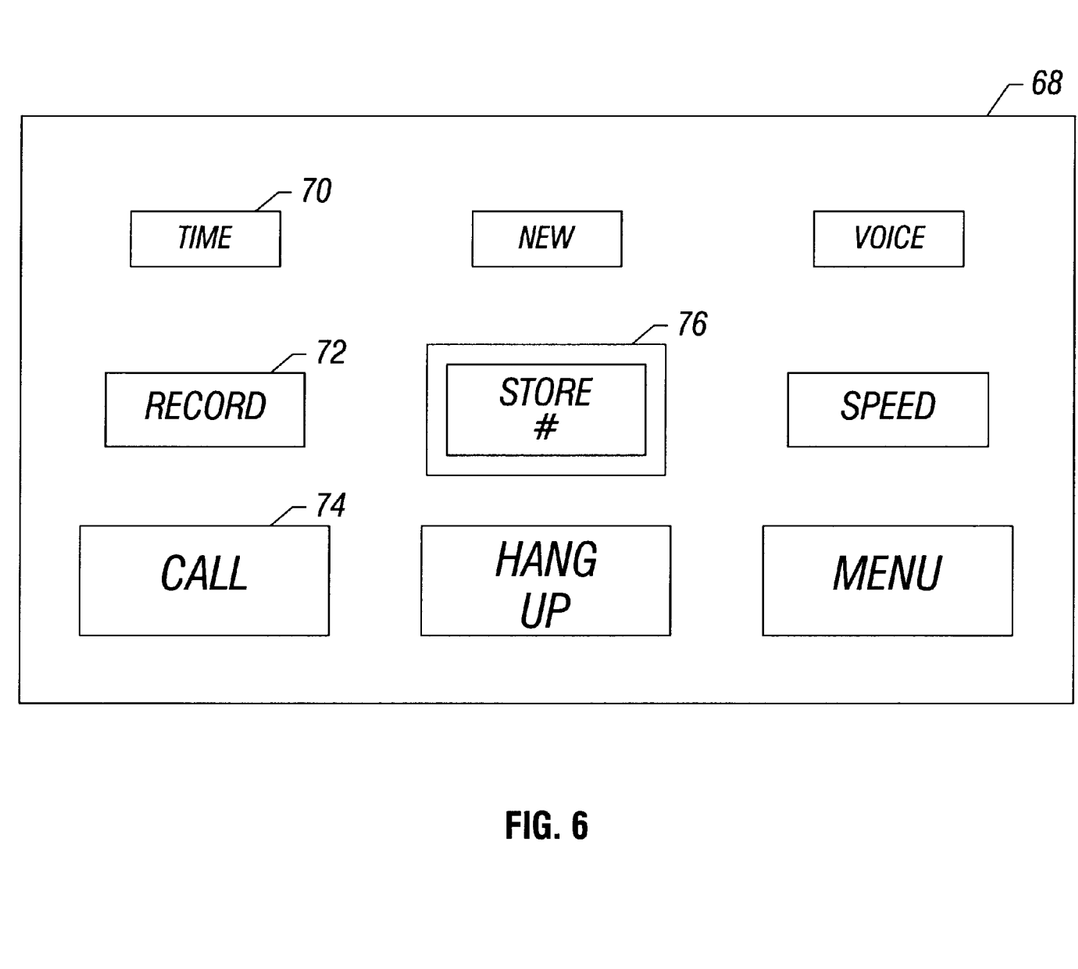
FIG. 6 is a screen display that may be utilized with one embodiment of the present invention.

Referring to FIG. 6, an exemplary microdisplay screen 68 is shown, which may include a plurality of graphical user interface icons 70, 72, 74 and 76. In the embodiment in which the electronic device 10 is a cellular telephone, the icons 70, 72, 74 may be provided to enable the user to initiate a call, to hang up a call, or to select a menu of items. Icons 74 for the most important items may be shown in the foreground of the display, in larger size. Icons 72 and 70 for items that amount to submenu possibilities may be aligned above a particular icon 74 and shown in progressively smaller size. For example, the call icon 74 is in the foreground and enlarged whereas the record 72 and time 70 icons are aligned above the call icon 74 and are progressively smaller in size.

Figure 7:
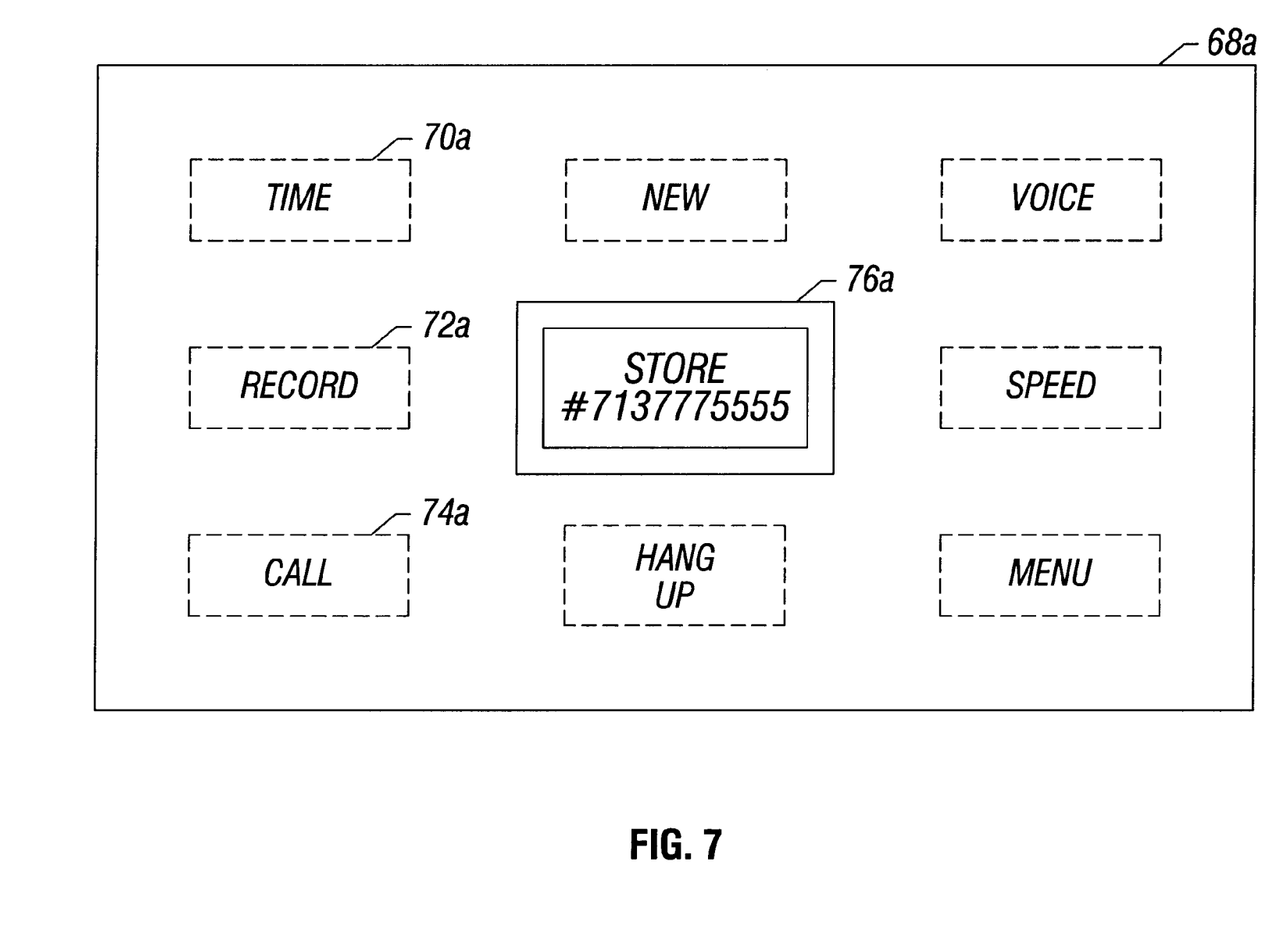
FIG. 7 is another screen display in accordance with an embodiment of the present invention.

In FIG. 6, the user has gazed on the icon 76 that has been highlighted (indicated by the double line) in response to the user's gaze. As a result of the user's selection of the icon 76, a new display screen 68a may be viewed, as indicated in FIG. 7. In this case, the microdisplay screen 68a has been altered so that the icon 76a has been enlarged and has been brought into clear focus. In addition, the particular telephone number which the user desires to store, is displayed in the enlarged icon 76a. Conversely, all the other displayed items have been automatically blurred and have been taken out of focus relative to the icon 76a, as indicated by their reduced size and by dashed lines in FIG. 7. Thus, in relation to the selected image element, the non-selected image elements may be reduced in size and may be physically blurred.

Figure 8:
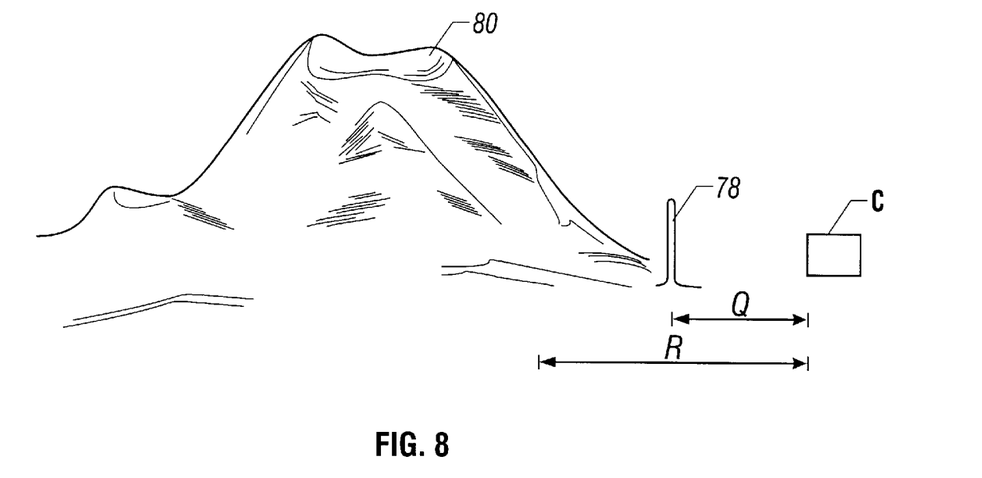
FIG. 8 is still another screen display in accordance with one embodiment of the present invention.

Objects 78 and 80 are viewed by a camera C as shown in FIG. 8. The distance of each object 78 and 80 from the camera C is designated as distances "Q" and "R", respectively.

Figure 9:
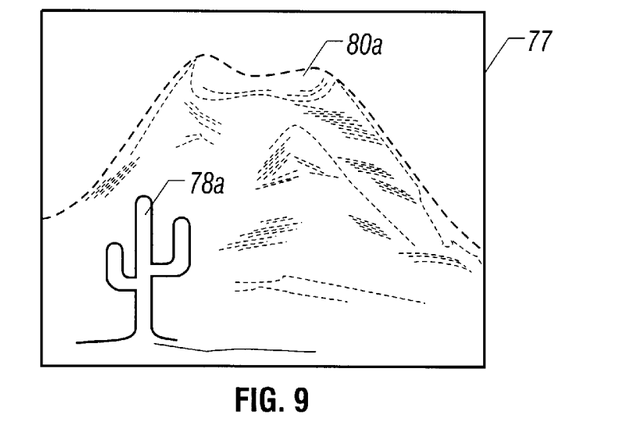
FIG. 9 is another screen display in accordance with one embodiment of the present invention.

A display screen 77, shown in FIG. 9, displays the image elements 78a and 80a of the objects 78 and 80 captured by the camera C. If the user gazes on the image element 78a, as displayed on the microdisplay 16, the depth of field of the screen 77 may automatically shift to center around image element 78a. As a result, image element 78a may be in clear and in focus, as indicated by solid lines. Conversely, the image element 80a may be depicted as =extending beyond the far boundary of the depth of field. As a result, the image element 80a may be blurred and presented as out of focus, as indicated by the dashed lines in FIG. 9.

Figure 10:
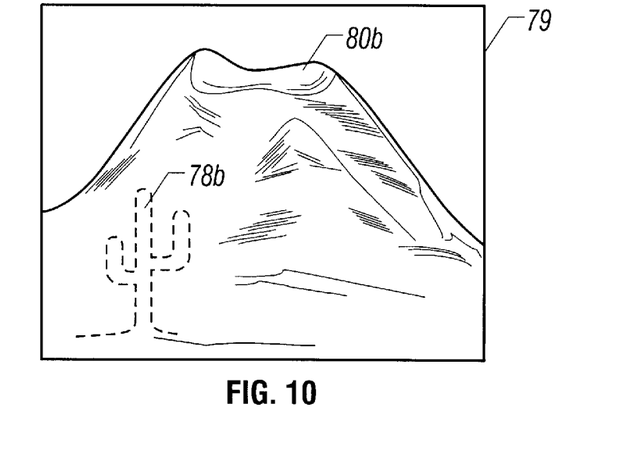
FIG. 10 is another screen display in accordance with one embodiment of the present invention.

A display screen 79 may result when the user gazes on the image element 80b instead of the image element 78a. In this case, the depth of field may be centered around the image element 80b, bringing it into clear focus (as indicated by solid lines). Because image element 78b may be depicted as being outside of the near boundary of the depth of field, it may be blurred and appear out of focus (as indicated by dashed lines).

In sum, the user may view a two-dimensional image element of a three dimensional scene. The depth of field of the scene, and hence the in-focus image element, may be determined to be image element the user gazes upon.

Figure 11:
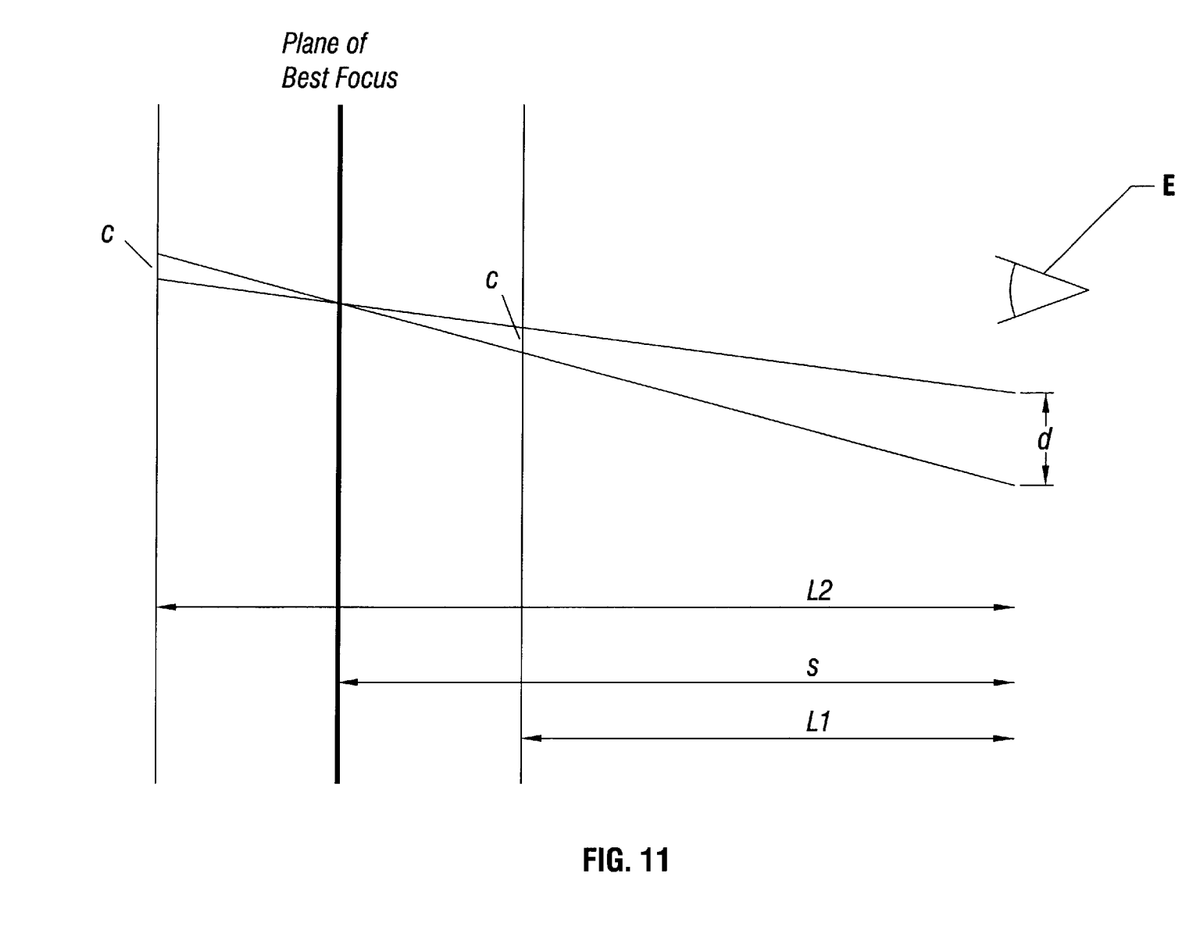
FIG. 11 is a diagram showing how the microdisplay may display one element in clear focus and other elements deliberately blurred in accordance with one embodiment of the invention.

The blurring operation, illustrated in FIG. 11, may be implemented by the depth calculation module 37. The user's eye E is at a distance "s" (from the entrance pupil of the eye's lens) to the "best plane of focus". The distance "L2" is the distance to the far boundary of what is perceived to be sharp. The distance "L1" is the distance to the near boundary of what is perceived to be sharp. The distance "d" is the diameter of the lens aperture, (its focal length divided by the F number). The letter "c" indicates the circle of confusion in the object plane. The circle of confusion is the size of a circle that is indistinguishable from a true point by the human eye. Typically, it is in the range of 1.5 to 3.4 minutes of arc depending on the viewing conditions and observer acuity.

From simple geometry then L2 is equal to sd/(d−c) and L1 is equal to sd/(d+c). Any pixels in the image element with a z value distance falling between L1 and L2 need not be modified as they would be perceived as being sharp by someone viewing the scene in person. Pixels with z values in the front or back of the desired focus plane may need to be blurred based on their distance from the plane of focus.

The amount of blur can be calculated by geometry. Any point appears to the eye spread to the diameter in which it intercepts the plane of best focus. A point at a distance L3 appears with the blur circle diameter c' as shown at the plane of best focus in FIG. 12. Thus, a digital image element blur filter may be applied to the pixels at plane L3 to render them for proper appearance. Any conventional blur filter function may be used here such as a neighborhood averaging, low pass filtering or the like.

Figure 12:
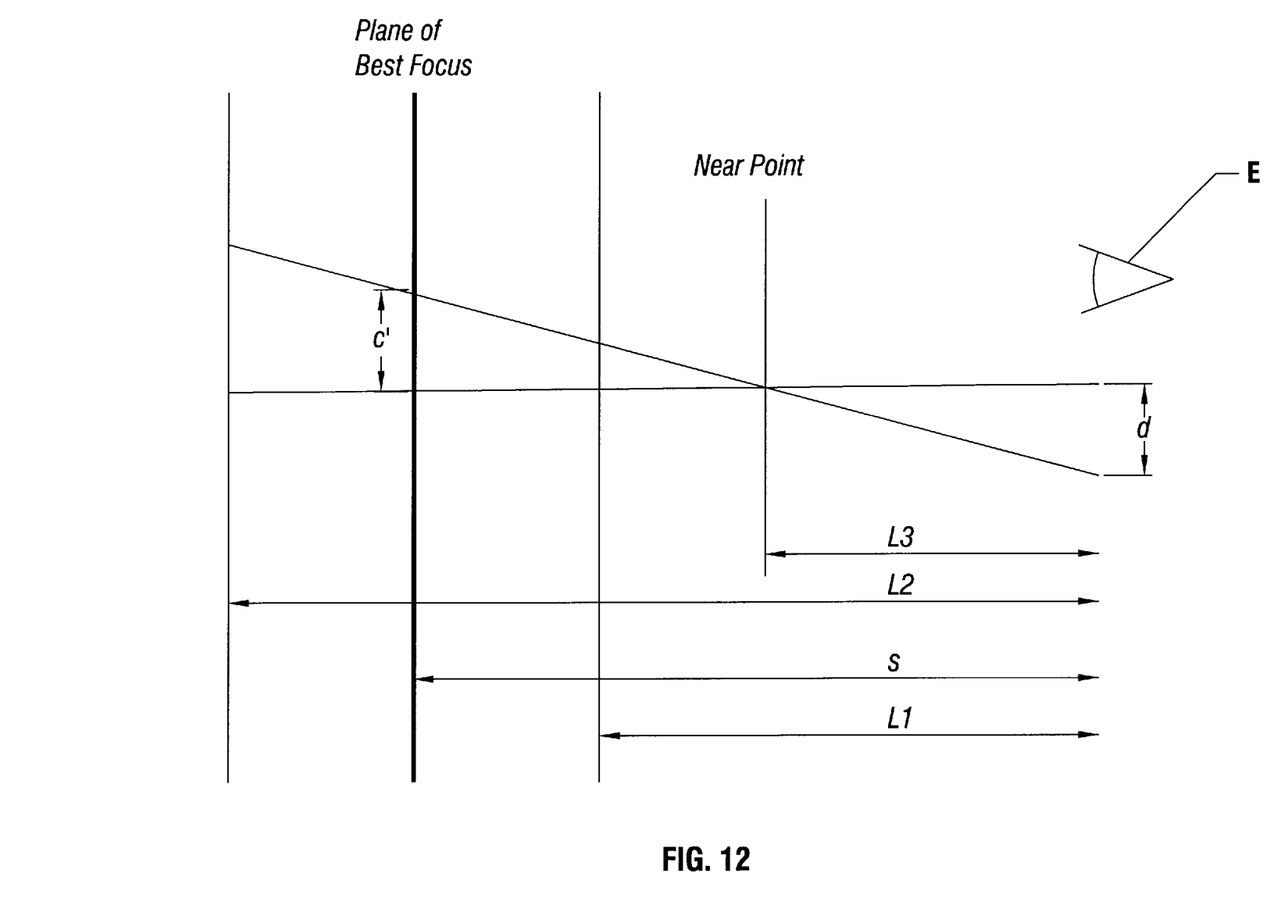
FIG. 12 is a schematic depiction of the user's eye relative to its plane of focus.

The radius of pixels to be used in an averaging function can be readily correlated to the blur transform of the original dot or line pair. Thus, blur functions can be designed with calibrated impact. As result, a look up table may be utilized to expedite the processing. In summary, the distance in z values of a pixel in the focus plane can be used as an index into a look up table to access the blur function control parameter needed to achieve the desired blur appearance.

Figure 13:
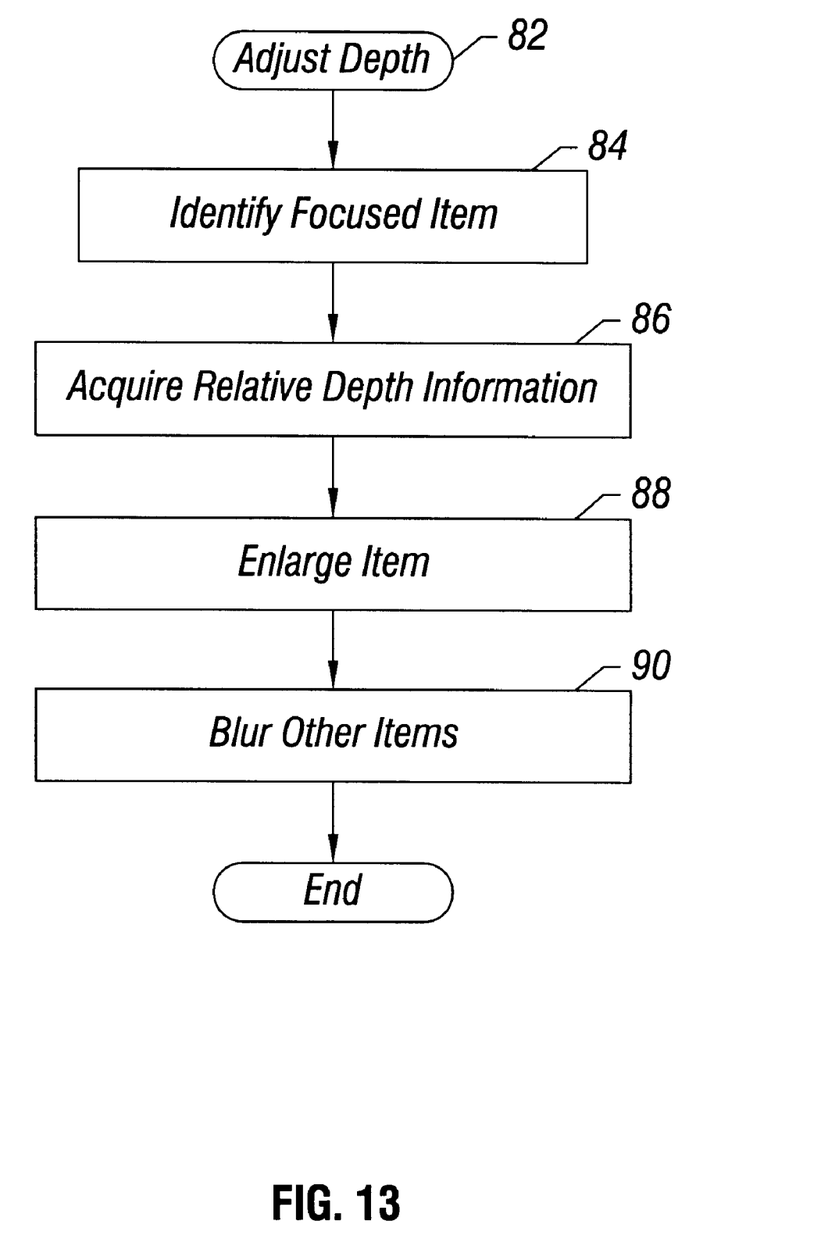
FIG. 13 is a flow chart for software in one embodiment of the present invention.

Referring to FIG. 13, software 82 may be utilized to accomplish the adjustment in the depth of field, according to one embodiment of the present invention. Initially, the image element that is the object of the user's gaze is identified using the eye gaze module 34 and gaze resolution module 36 as indicated in block 84. The relative depth information is acquired (block 86). The subject image element is brought into clear focus, as indicated in block 88, and may be enlarged. The other image elements are subjected to digital processing, using software 114, to blur them as described above and as indicated in block 90.

Figure 14:
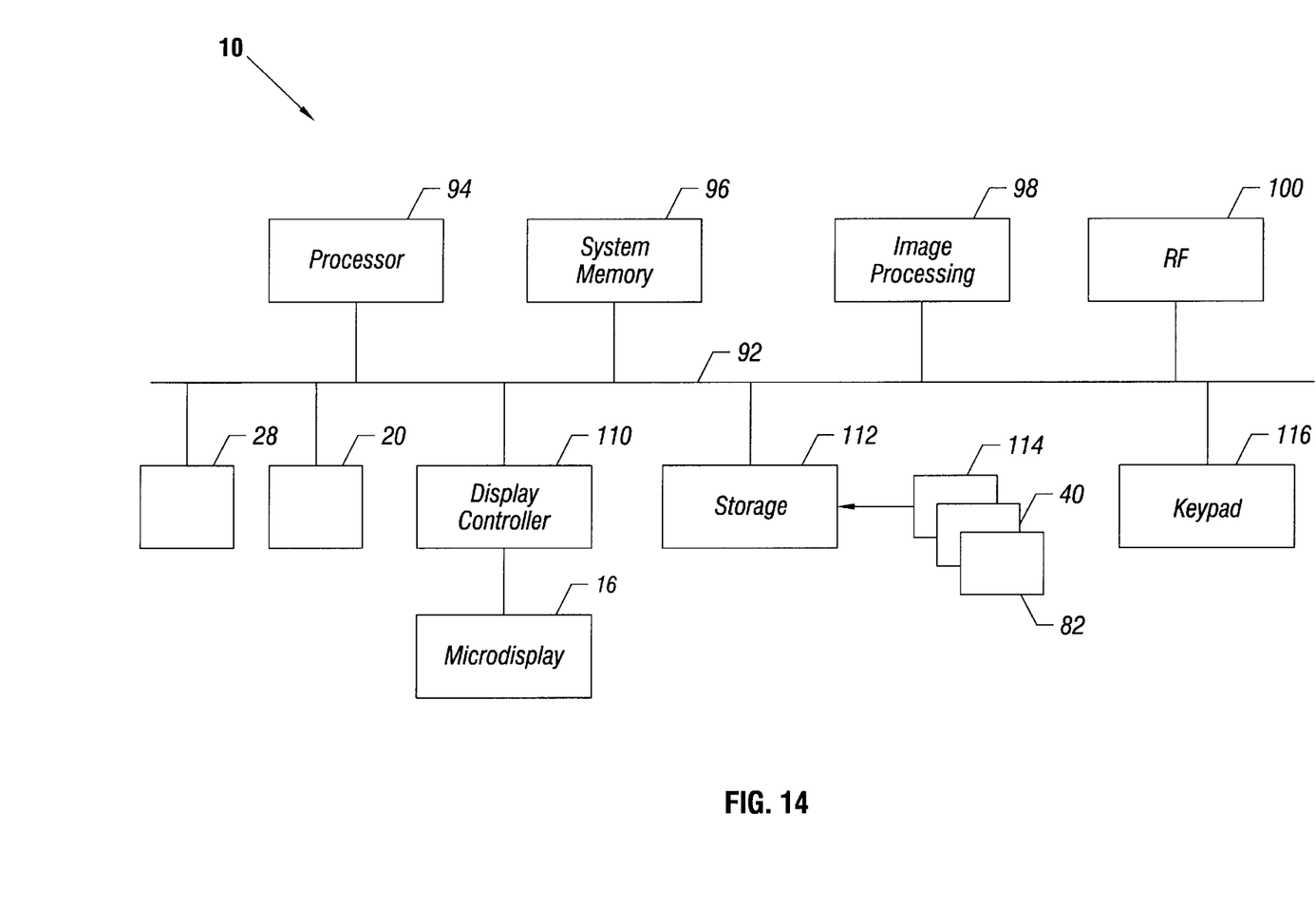
FIG. 14 is a block diagram showing hardware for one embodiment of the present invention.

Referring to FIG. 14, in one embodiment of the present invention, the electronic device 10 is a cellular telephone. The device 10 includes a bus 92 that couples a processor 94 and a system memory 96. In one embodiment, the processor 94 may execute the software modules 34, 36 and 37 of FIG. 4. An image element processing device 98 may likewise be coupled to the bus 92 together with a radio frequency (RF) processing chip device 100. The device 98 may be used for image element processing tasks including implementing the blur function.

The infrared eye illuminators 28 and infrared imaging subsystem 20 may also be coupled to the bus 92. The display controller 110 may be coupled to the microdisplay 16 and the bus 92. A storage device 112, coupled to the bus 92, may be a semiconductor storage such as a flash memory. It may store the software 40 and 82 in accordance with one embodiment of the present invention. In addition, the storage device 112 may store software 114 for implementing the blur function and the blur function lookup table. A keypad 116 for manual entry may be provided as well. Other components such as microphones, and the like are omitted for clarity purposes.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A system comprising:
   a microdisplay;
   an eye gaze detector to detect an image element a user is looking at displayed on said microdisplay; and
   a device coupled to said detector and said display to automatically alter the appearance of the image element the user is looking at in a first way by causing the image element to be enlarged relative to other displayed image elements and to automatically alter the appearance of another image element displayed on said microdisplay in a second way different from said first way by causing the other image element to be reduced in size relative to the image element the user is looking at.

2. The system of claim 1 further including a timer to time the user's gaze at said image element, said image element and said other image element being computer generated image elements and said microdisplay to automatically alter the appearance of said image element and said other element in response to the timing of the user's gaze.

3. The system of claim 1 wherein said timer continues to time the user's gaze at said altered image element and said microdisplay to automatically change the content displayed on said microdisplay in response to the continued timing of the user's gaze.

4. A system comprising:
   a microdisplay;
   an eye gaze detector to detect an image element a user is looking at displayed on said microdisplay; and
   a device coupled to said detector and said display to automatically alter the appearance of the image element the user is looking at in a first way by centering the depth of field at said image element and to automatically alter the appearance of another image element displayed on said microdisplay in a second way different from said first way by blurring the other image element.

5. The system of claim 4 wherein said eye gaze detector includes an infrared light source to reflect light from the user's eye and an infrared imaging subsystem to capture and record an image of the user's eye.

6. The system of claim 5 wherein said eye gaze detector includes a processor to track features of the user's eye and spatially resolve what the user is looking at.

7. The system of claim 6 wherein the image elements displayed on the microdisplay define visual points of interest.

8. The system of claim 7 wherein said eye gaze detector includes a gaze resolution module to determine whether the image element the user is looking at is coincident with a visual point of interest.

9. The system of claim 4 further including a timer to time the user's gaze at said image element, said image element and said other image element being computer generated image elements and said display to automatically alter the appearance of said image element and said other element in response to the timing of the user's gaze.

10. The system of claim 9 wherein said timer continues to time the user's gaze at said altered image element and said microdisplay to automatically change the content displayed on said microdisplay in response to the continued timing of the user's gaze.

11. An article comprising a medium storing instructions that enable a processor-based system to:
    detect an image element that a user is looking at displayed on a microdisplay;
    automatically alter the appearance of the image element the user is looking at in a first way by causing the image element to be more enlarged and focused relative to another display image element; and
    automatically alter the appearance of the other image element displayed on said microdisplay in a second way that is different from said first way by causing the other image element to be reduced and blurred.

12. The article of claim 11 further storing instructions that enable a processor-based system to time the user's gaze at said image element, said image element and said other image element being computer generated image elements and alter the appearance of said image element and said other image element in response to the timing of the user's gaze.

13. The article of claim 12 further storing instructions that enable a processor-based system to continue to time the user's gaze at said altered image element and change the content displayed on said microdisplay in response to the continued timing of the user's gaze.

14. An article comprising a medium storing instructions that enable a processor-based system to:
    detect an image element that a user is looking at displayed on a microdisplay;
    automatically alter the appearance of the image element the user is looking at in a first way by centering the depth of field for the display around the image element that the user is looking at; and
    automatically alter the appearance of another image element displayed on said microdisplay in a second way that is different from said first way by blurring the other displayed image element.

15. The article of claim 14 further storing instructions that enable a processor-based system to spatially resolve what the user is looking at by detecting infrared light reflected off the user's eye.

16. The article of claim 14 further storing instructions that enable a processor-based system to detect the image element the user is looking at by comparing said image element to a known point of activation.

17. The article of claim 14 further storing instructions that enable a processor-based system to time the user's gaze.

18. The article of claim 17 further storing instructions that enable a processor-based system to alter the appearance of an image element displayed on the microdisplay in response to the time the user gazes at the image element.

19. The article of claim 18 further storing instructions that enable a processor-based system to continue to time the user's gaze at said image element, said image element and said other image element being computer generated image elements and change the content displayed on said microdisplay in response to the continued timing of the user's gaze.

20. A method comprising:
    detecting an image element displayed on a microdisplay that a user is looking at;
    automatically altering the appearance of the image element the user is looking at in a first way by centering the depth of field around an image element displayed on the microdisplay after the user has looked at said image element; and automatically altering the appearance of another image element displayed on the microdisplay in a second way that is different from said first way by blurring the appearance of the other image element displayed on the microdisplay.

21. The method of claim 20 wherein detecting the image element that the user is looking at includes resolving what the user is looking at by using an infrared light source to reflect light from the user's eye and by using an infrared imaging subsystem to capture and record the user's eye image.

22. The method of claim 20 wherein detecting the image element that the user is looking at includes comparing said image element with a known activation point's coordinates.

23. The method of claim 20 including timing the user's gaze.

24. The method of claim 23 wherein altering the appearance of the image element in the first way and altering the appearance of the another image element in the second way are in response to the timing of the user's gaze.

25. The method of claim 24 further including continuing timing the user's gaze at said image element, said image element and said other image element being computer generated elements and changing the content displayed on said microdisplay in response to the continued timing of the user's gaze.

26. A method comprising:

detecting an image element displayed on a microdisplay that a user is looking at;

automatically altering the appearance of the image element the user is looking at in a first way by enlarging the image element and placing the image element in focus relative to another image element on the display; and automatically altering the appearance of another image element displayed on the microdisplay in a second way that is different from said first way by reducing and blurring the other image element.

27. The method of claim 26 further including timing the user's gaze at said image element, said image element and said other image elements being computer generated image elements and altering the appearance of said image element and said other image element in response to the timing of the user's gaze.

28. The method of claim 27 further including continuing timing the user's gaze at said image element and changing the content displayed on said microdisplay in response to the continued timing of the user's gaze.

* * * * *